(12) United States Patent
Menn et al.

(10) Patent No.: US 9,468,452 B2
(45) Date of Patent: *Oct. 18, 2016

(54) SPECIMEN RETRIEVAL DEVICE

(71) Applicant: Covidien LP, Mansfield, MA (US)

(72) Inventors: Dmitri Menn, Marblehead, MA (US);
Gene A. Stellon, Burlington, CT (US)

(73) Assignee: Covidien LP, Mansfield, MA (US)

( * ) Notice: Subject to any disclaimer, the term of this patent is extended or adjusted under 35 U.S.C. 154(b) by 249 days.

This patent is subject to a terminal disclaimer.

(21) Appl. No.: 14/047,451

(22) Filed: Oct. 7, 2013

(65) Prior Publication Data

US 2014/0058403 A1  Feb. 27, 2014

Related U.S. Application Data

(63) Continuation of application No. 13/325,523, filed on Dec. 14, 2011, now Pat. No. 8,579,914.

(60) Provisional application No. 61/424,240, filed on Dec. 17, 2010.

(51) Int. Cl.
 *A61B 17/221* (2006.01)
 *A61B 17/00* (2006.01)
 (Continued)

(52) U.S. Cl.
 CPC ....... *A61B 17/221* (2013.01); *A61B 17/00234* (2013.01); *A61B 2017/00287* (2013.01);
 (Continued)

(58) Field of Classification Search
 CPC .......... A61B 17/00234; A61B 17/221; A61B 2017/00287; A61B 2017/00853; A61B 2017/2212; A61B 2017/2215; A61B 2017/320064; A61B 10/02; A61B 10/0096; A61B 10/007; A61F 5/44; A61F 5/451; A61F 5/453; A61F 13/471; A61F 6/04; A61F 6/065; A61F 2006/045–2006/048
 USPC ......... 606/114, 127–128; 600/562, 580, 582; 206/361, 305, 438; 604/163, 164.08, 604/164.12, 177, 271, 327–328, 347, 349; 128/842, 844
 See application file for complete search history.

(56) References Cited

U.S. PATENT DOCUMENTS

| | | | |
|---|---|---|---|
| 30,471 A | 10/1860 | Dudley | |
| 35,164 A | 5/1862 | Logan et al. | |

(Continued)

FOREIGN PATENT DOCUMENTS

| | | |
|---|---|---|
| DE | 8435489 | 12/1984 |
| DE | 3542667 | 6/1986 |

(Continued)

OTHER PUBLICATIONS http://www.biomaterials.org/week/bio17.cfm, Definition of Hydrogels, retrived Jan. 6, 2013.*

(Continued)

*Primary Examiner* — David C Eastwood

(57) ABSTRACT

A specimen retrieval device is provided. The specimen retrieval device includes an applicator. A specimen retrieval pouch operably is disposed within the applicator and deployable therefrom. The specimen retrieval pouch defines a longitudinal axis therethrough and includes a closed bottom portion and an open upper portion. The closed bottom portion includes a plurality of spikes configured to grasp a specimen positioned within the confines closed bottom portion. The upper closed portion includes one or more axial folds that are movable from a folded configuration to an unfolded configuration when a predetermined force is applied to a portion of the specimen retrieval pouch.

12 Claims, 6 Drawing Sheets

(51) Int. Cl.
  *A61B 17/29* (2006.01)
  *A61B 17/32* (2006.01)
(52) U.S. Cl.
  CPC ............... *A61B2017/00473* (2013.01); *A61B 2017/00853* (2013.01); *A61B 2017/00862* (2013.01); *A61B 2017/00907* (2013.01); *A61B 2017/2911* (2013.01); *A61B 2017/320064* (2013.01)

(56) References Cited

U.S. PATENT DOCUMENTS

| | | |
|---|---|---|
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | Levahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A * | 5/1994 | Spaeth et al. ............... 606/114 |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,383,888 A | 1/1995 | Zvenyatsky et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,578,048 A | 11/1996 | Pasqualucci et al. |
| 5,611,803 A | 3/1997 | Heaven et al. |
| 5,618,294 A | 4/1997 | Aust et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A * | 4/1999 | Riek et al. ............... 606/114 |
| 5,906,621 A | 5/1999 | Secrest et al. |
| 5,908,429 A | 6/1999 | Yoon |
| 5,944,727 A | 8/1999 | Ahari et al. |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternström |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,325,546 B2 | 2/2008 | Burbank et al. |
| 7,410,491 B2 | 8/2008 | Hopkins et al. |
| 7,547,310 B2 | 6/2009 | Whitfield |
| 7,670,346 B2 | 3/2010 | Whitfield |
| 7,762,959 B2 | 7/2010 | Bilsbury |
| 7,819,121 B2 | 10/2010 | Amer |
| 8,579,914 B2 * | 11/2013 | Menn et al. ............... 606/114 |
| 2003/0100909 A1 | 5/2003 | Suzuki |
| 2004/0097960 A1 | 5/2004 | Terachi et al. |
| 2004/0138587 A1 | 7/2004 | Lyons |
| 2005/0165411 A1 | 7/2005 | Orban, III |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0199999 A1 | 9/2006 | Ikeda et al. |
| 2006/0200169 A1 | 9/2006 | Sniffin |

(56) References Cited

U.S. PATENT DOCUMENTS

| | | |
|---|---|---|
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0177214 A1 | 7/2008 | Robertsson et al. |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300613 A1 | 12/2008 | Shelton et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0192518 A1 | 7/2009 | Golden et al. |
| 2009/0240238 A1 | 9/2009 | Grodrian et al. |
| 2010/0000471 A1 | 1/2010 | Hibbard |
| 2011/0184434 A1* | 7/2011 | Parihar et al. ............. 606/114 |
| 2011/0184436 A1 | 7/2011 | Shelton, IV et al. |
| 2011/0190781 A1 | 8/2011 | Collier et al. |
| 2011/0299799 A1 | 12/2011 | Towe |
| 2012/0046667 A1 | 2/2012 | Cherry |
| 2012/0083795 A1 | 4/2012 | Fleming |
| 2013/0023895 A1 | 1/2013 | Saleh |

FOREIGN PATENT DOCUMENTS

| | | |
|---|---|---|
| DE | 4204210 | 8/1992 |
| DE | 19624826 | 1/1998 |
| EP | 0947166 | 10/1999 |
| EP | 1685802 | 8/2006 |
| EP | 1707126 | 10/2006 |
| EP | 2005900 A2 | 12/2008 |
| EP | 2184014 | 5/2010 |
| EP | 2353510 | 8/2011 |
| FR | 1272412 | 9/1961 |
| GB | 2460099 | 11/2009 |
| WO | WO 93/15675 | 8/1993 |
| WO | WO 95/09666 | 4/1995 |
| WO | WO 01/35831 | 5/2001 |
| WO | WO 2004/002334 | 1/2004 |
| WO | WO 2004/112571 | 12/2004 |
| WO | WO 2005/112783 A1 | 12/2005 |
| WO | WO 2006/110733 | 10/2006 |
| WO | WO2007/048078 | 4/2007 |
| WO | WO2007/048085 | 4/2007 |
| WO | WO 2008/114234 | 9/2008 |
| WO | WO2009/055791 | 4/2009 |
| WO | WO2009/149146 | 12/2009 |
| WO | WO2011/090862 | 7/2011 |

OTHER PUBLICATIONS

Partial International Search Report corresponding to EP No. 12 19 1639.9, mailed Feb. 20, 2013; (6 pp).
Extended European Search Report corresponding to EP No. 11 25 0837.9, completed Sep. 3, 2013 and mailed Sep. 10, 2013; (7 pp).
Extended European Search Report corresponding to EP No. 11 25 0838.7, completed Sep. 3, 2013 and mailed Sep. 10, 2013; (5 pp).
Extended European Search Report corresponding to EP No. 13 17 0118.7. completed Nov. 25, 2013 and mailed Dec. 5, 2013; (10 pp).
International Search Report corresponding to European Application No. EP 12 16 5852 completed Jun. 13, 2012 and mailed Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report EP 11250114.3 dated Feb. 10, 2014.

* cited by examiner

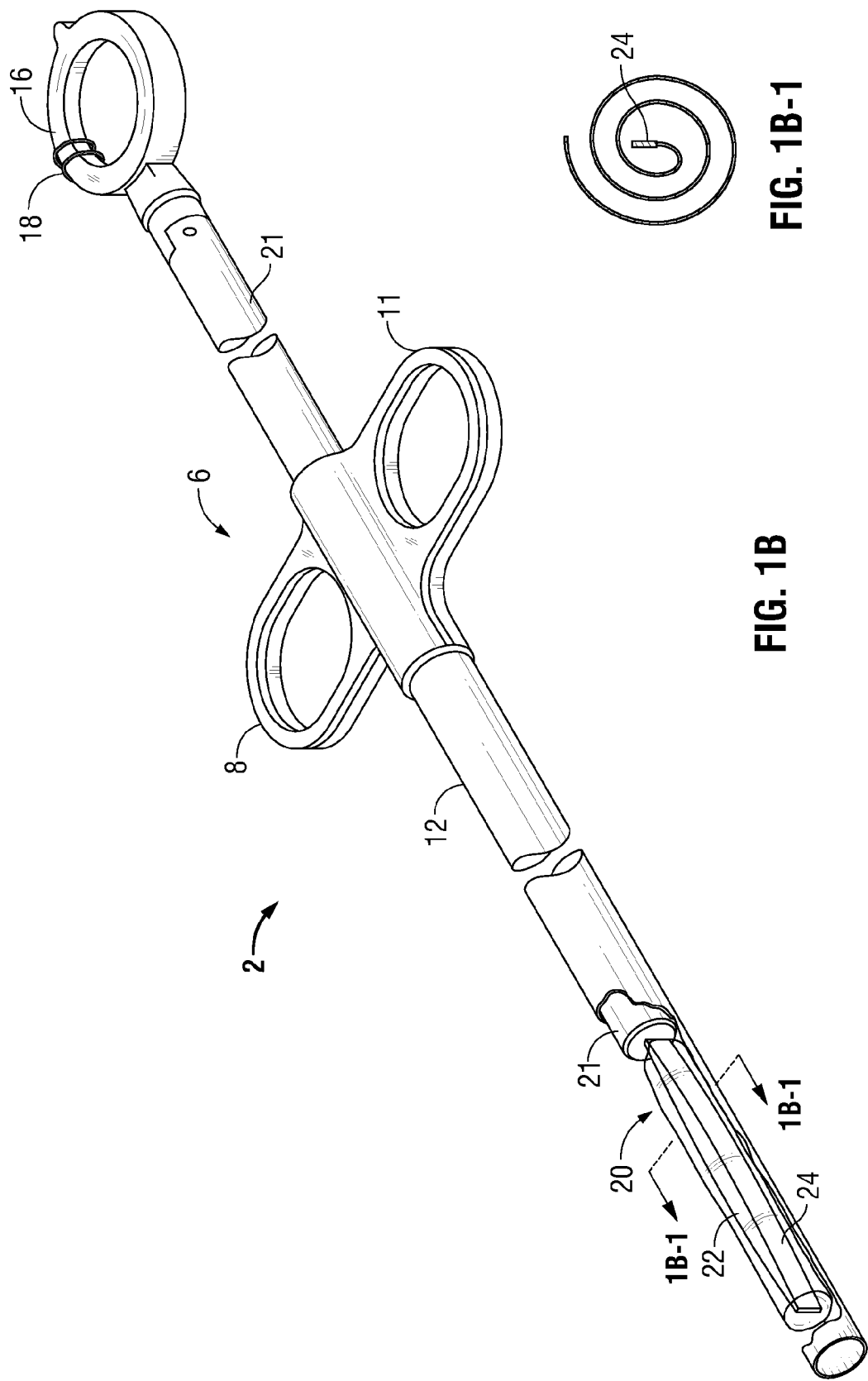

SPECIMEN RETRIEVAL DEVICE

CROSS-REFERENCE TO RELATED APPLICATIONS

The present application is a continuation application of U.S. patent application Ser. No. 13/325,523 filed by Menn et al. on Dec. 14, 2011, which claims the benefit of and priority to U.S. Provisional Patent Application No. 61/424,240 filed by Menn et al. on Dec. 17, 2010 the entirety of each of these applications being incorporated herein by reference.

BACKGROUND

1. Technical Field

The present disclosure relates to a specimen retrieval device. More particularly, the present disclosure relates to a specimen retrieval device configured for use in minimally invasive surgical procedures.

2. Background of Related Art

Laparoscopic and endoscopic surgical procedures are minimally invasive procedures in which operations are carried out within the body by means of elongated instruments inserted through small entrance or access openings in the body, e.g., an opening defined by a natural passageway of the body, an opening created by a tissue piercing instrument (e.g., a trocar), etc.

Minimally invasive procedures are often used to partially or totally remove body tissue or organs from the interior of the body, e.g. nephrectomy, cholecystectomy, duodenectomy, ileectomy, jejunectomy and other such procedures. During such procedures, it is common that affected tissue or organ must be removed via the access opening in the skin, or through a cannula. Various types of entrapment devices are known in the art to facilitate this procedure.

For example, a specimen retrieval bag including a morcellation means configured to percutaneously debulk tissue may be utilized. Typically, the specimen retrieval bag includes a layer of puncture-resistant material, a layer of moisture-resistant material, a morcellator, and a drawstring. In use, the specimen retrieval bag is placed within a body cavity. The body tissue or organ is placed within the specimen retrieval bag. The morcellator chops or otherwise treats the tissue or organ (in certain instances portions of the chopped tissue or organ may be suctioned out of the specimen retrieval bag). Thereafter, the specimen retrieval bag may be pulled out of the body cavity through the incision in the skin.

In another example, a specimen retrieval device may include planar membrane having filaments attached to its corners. In use, the membrane is placed within a body cavity with the filaments extending through the trocar cannula to the outside of the body. In the instance where the organ or tissue of interest is sufficiently deformable, the tissue of interest is placed on the membrane and the filaments are pulled to close the membrane around the organ and draw it through the cannula. In the instance where the organ is not sufficiently deformable, e.g. because of the presence of gall stones, a forceps or other instrument may be used to crush the stones or tissue.

Although specimen retrieval devices, such as those described above, are known, there remains a need for an improved specimen retrieval device that is configured to facilitate tissue removal in minimally invasive surgical procedures, especially in this instance where longer length tissue needs to be removed.

SUMMARY

The present disclosure provides a specimen retrieval device. The specimen retrieval device includes an applicator. A specimen retrieval pouch operably is disposed within the applicator and deployable therefrom. The specimen retrieval pouch defines a longitudinal axis therethrough and includes a closed bottom portion and an open upper portion. The closed bottom portion includes a plurality of spikes configured to enagage a specimen positioned within the confines of the closed bottom portion. The open upper portion includes one or more axial folds that are movable from a folded configuration to an unfolded configuration when a predetermined force is applied to a portion of the specimen retrieval pouch.

The present disclosure provides a specimen retrieval pouch configured for use with an applicator. The specimen retrieval pouch is adapted to couple to the applicator and is deployable therefrom. The specimen retrieval pouch defines a longitudinal axis therethrough and includes a closed bottom portion and an open upper portion. The closed bottom portion includes a plurality of spikes configured to engage a specimen positioned within the confines of the closed bottom portion. The open upper portion includes one or more axial folds that are movable from a folded configuration to an unfolded configuration when a predetermined force is applied to a portion of the specimen retrieval pouch.

BRIEF DESCRIPTION OF THE DRAWINGS

Embodiments of the presently disclosed specimen retrieval apparatus are described hereinbelow with reference to the drawings wherein.

Figure 1A:
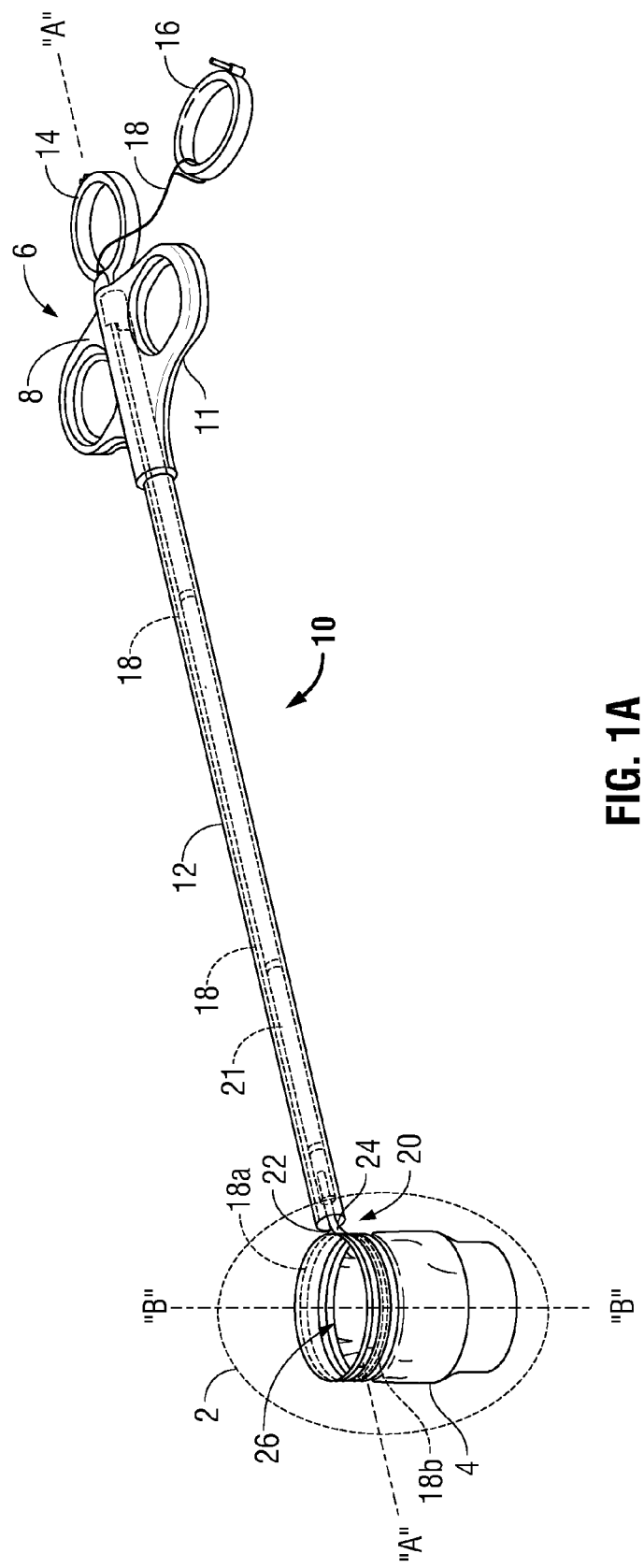
FIG. 1A is a perspective view of a specimen retrieval device with a specimen retrieval pouch in a folded configuration and deployed state in accordance with the present disclosure.
Figure 1C:
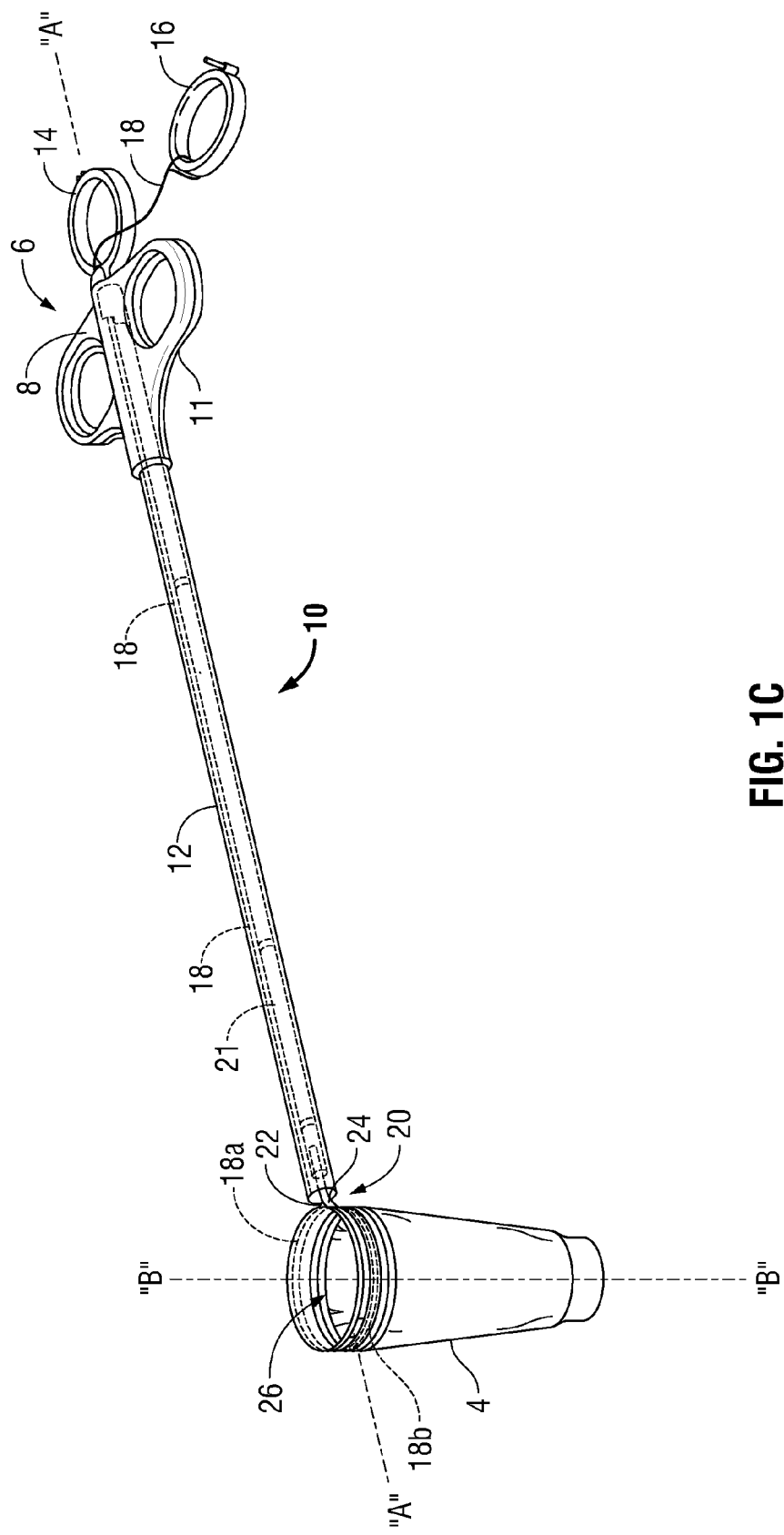
FIG. 1B is a perspective view of the specimen retrieval device depicted in FIG. 1A with the specimen retrieval pouch in a folded configuration and non-deployed state.
Figure 2:
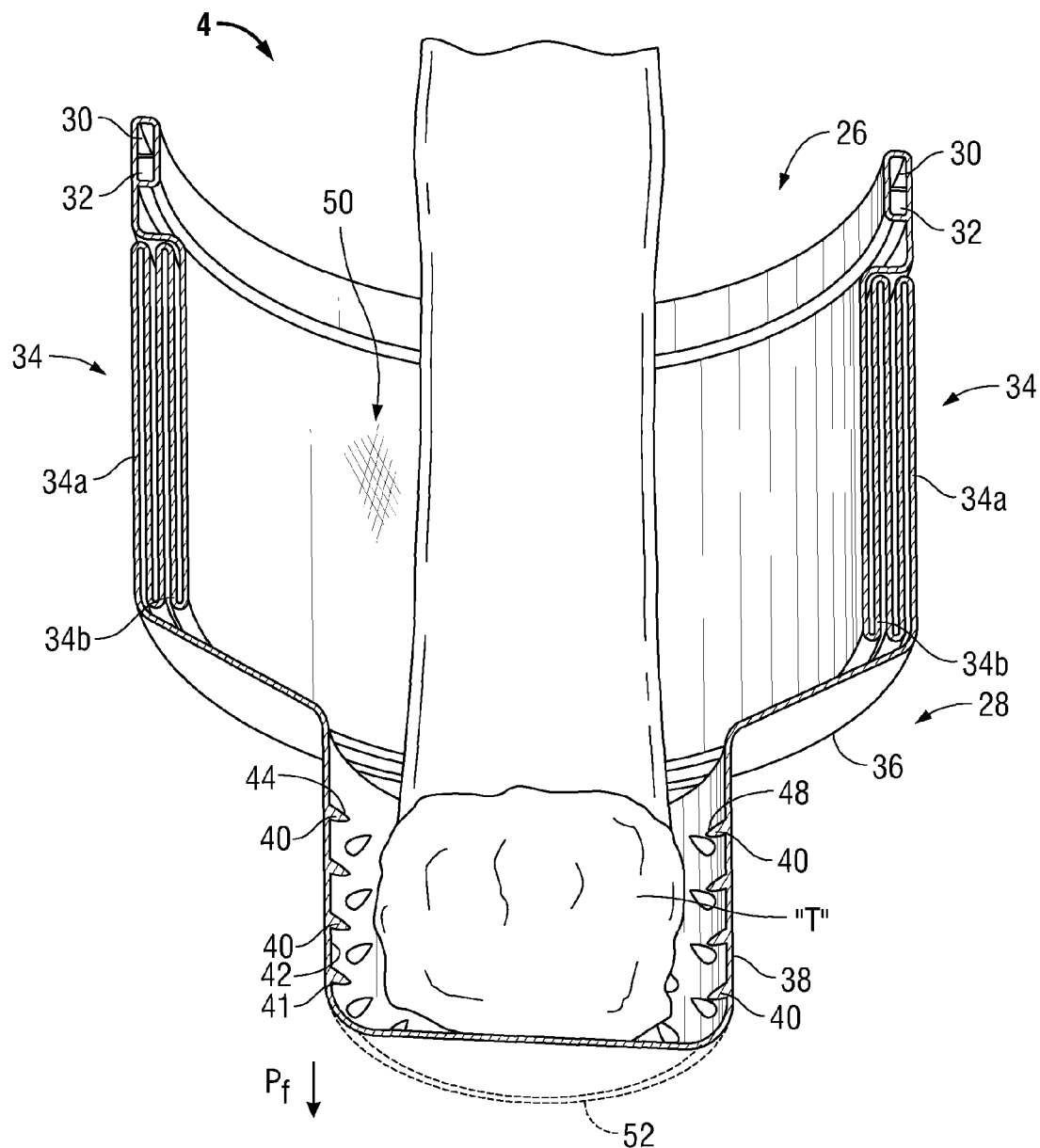
Figure 3:
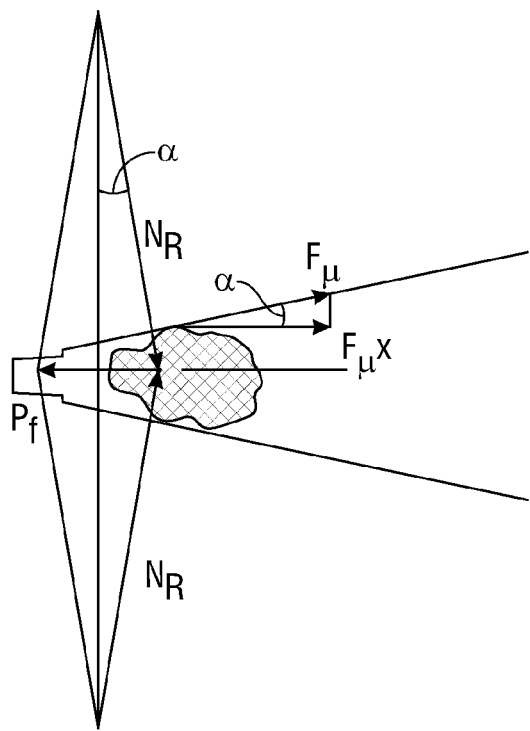
Figure 4:
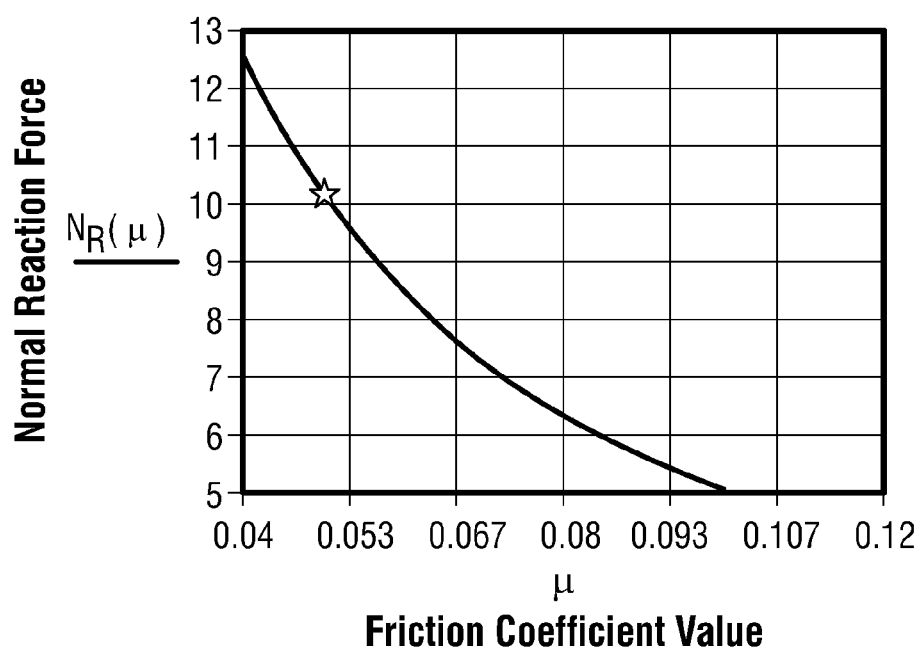
Figure 5:
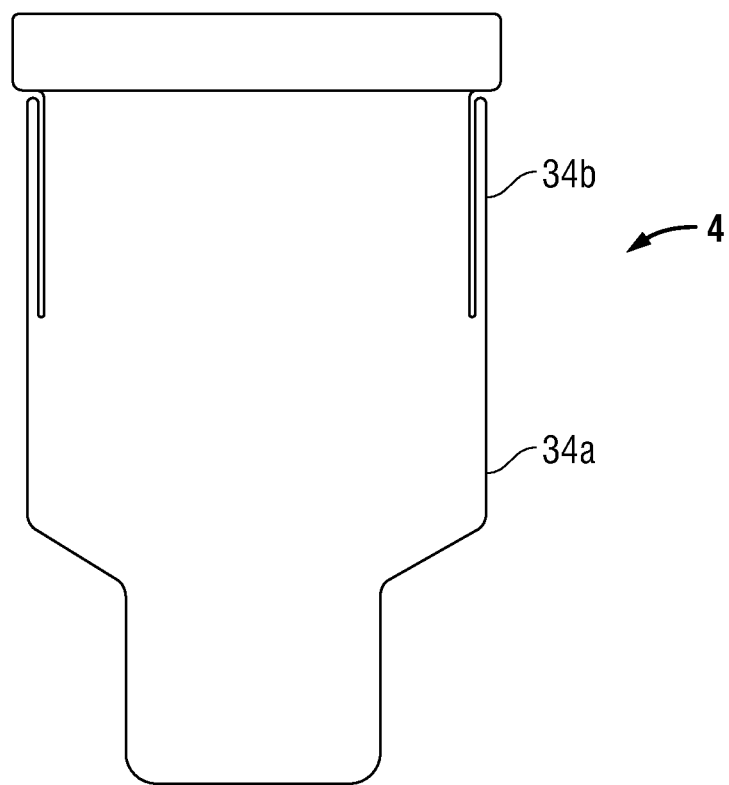

FIG. $1B_{-1}$ is a cross-sectional view taken along line segment "$1B_{-1}$-$1B_{-1}$" in FIG. 1B;

FIG. 1C is a perspective view of the specimen retrieval device depicted in FIG. 1A with the specimen retrieval pouch in an un-folded configuration and deployed state;

FIG. 2 is an enlarged cross-sectional view of the area of detail depicted in FIG. 1A;

FIG. 3 is a simplified force vector diagram illustrating a low friction effect associated with the specimen retrieval pouch depicted in FIGS. 1A-2;

FIG. 4 is a graphical representation of a normal reaction force as a function of a friction coefficient associated with an interior wall of the retrieval pouch; and FIG. 5 is a side view of the specimen retrieval pouch depicted in FIGS. 1A-2 with an outer axial fold in an unfolded condition.

DETAILED DESCRIPTION OF THE EMBODIMENTS

Embodiments of the present disclosure will now be described in detail with reference to the drawings, in which like reference numerals designate identical or corresponding elements in each of the several views. As used herein, the term distal refers to the portion of the instrument which is farthest from the user, while the term proximal refers to that portion of the instrument which is closest to the user. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures.

With reference to FIGS. 1A-1C, a specimen retrieval device 10 including a specimen retrieval pouch 4 (pouch 4) according to an embodiment of the present disclosure is illustrated.

Briefly, specimen retrieval device 10 includes a handle assembly 6 that includes handle portions 8 and 11 (FIG. 1A) that are fixedly joined together. An elongated tube or shaft 12 extends from the handle assembly 6 and is dimensioned for insertion through a trocar cannula for endoscopic or laparoscopic procedures (FIG. 1A). In certain embodiments, the shaft 12 may be configured to articulate. A longitudinal axis "A-A" is defined through the shaft 12 and is oriented in a substantially perpendicular or orthogonal direction with respect to a longitudinal axis "B-B" that is defined through the pouch 4 when the pouch 4 is in the deployed state (FIGS. 1A and 1C). A drive rod 21 extends within the shaft 12 and along a length thereof and operably couples to an actuator that is in the form of a finger loop 14 (FIGS. 1A and 1C). A distal end of the drive rod 21 operably couples to the pouch 4. Finger loop 14 is configured for engagement by a user's fingers and is configured to translate or move the drive rod 21 within the shaft 12. A pull ring 16 is operably coupled to a proximal end of a drawstring 18 by any suitable coupling method, e.g., tied, adhesive, etc., and is configured to facilitate pulling the drawstring 18 (FIG. 1A). In the illustrated embodiment, pull ring 16 releasably couples, via one or more suitable coupling methods, e.g., a press or friction fit, to the finger loop 14, see FIG. 1A in combination with FIG. 1B, for example. A distal end of the drawstring 18 includes two separate ends 18a and 18b that are operably coupled to a portion, e.g., an open upper portion 26, of the pouch 4, the significance of which is described in greater detail below. A deformable spring 20 operably couples to the drive rod 21 and includes two generally flexible or resilient strips 22 and 24 that move from a stressed or non-expanded state (FIG. 1B) to an unstressed or freely expanded state (FIG. 1A) when the pouch 4 is deployed from the shaft 12. In the stressed or non-expanded state, the pouch 4 is wound or wrapped around the resilient strips 22 and 24, see FIG. 1B$_1$ for example. Wrapping the pouch 4 around the resilient strips 22 and 24 facilitates deploying the pouch 4 from the relatively small area within the shaft 12. In an unstressed or freely expanded condition, the two resilient strips 22 and 24 collectively form a generally circular or "hoop-like" configuration for supporting a periphery of the opening 26 of pouch 4 (see FIG. 1A in combination with FIG. 1C).

For a more detailed description of the specimen retrieval device 10 and operative components associated therewith, reference is made to commonly-owned U.S. Pat. No. 5,647,372 to Tovey et al., filed on Sep. 16, 1994, the entirety of which being incorporated herein by reference.

Continuing with reference to FIGS. 1A-1C, and with particular reference to FIG. 2, pouch 4 is shown. Pouch 4 may be made from any suitable biocompatible materials capable of forming a flexible membrane. More particularly, pouch 4 includes a flexible film or sheet formed from a substantially transparent polymeric material. In the illustrated embodiment, the polymeric material is polyurethane sheet having a thickness that ranges from about 0.001 inches to about 0.005 inches. Pouch 4 is substantially impervious to penetration by cancer cells. Pouch 4 is proportioned for the purpose of organ entrapment or removal. In the illustrated embodiment, the pouch 4 includes a diameter that ranges from about 1.5 inches to about 3.0 inches and a changeable or variable depth that ranges from about 2 inches to about 8 inches. In certain instances, the pouch 4 may be dimensioned and fabricated of a suitable material to allow treatment, e.g. morcellation or division, of the organ tissue, for example to reduce its bulk to facilitate withdrawal from the body cavity.

Pouch 4 includes a generally tubular or elongated configuration that is defined by an openable and closable upper portion or mouth 26 and closed lower portion 28 (FIG. 2).

As best seen in FIG. 2, upper portion 26 includes is a proximal (or upper) circumferential tubular portion or sleeve 30, and a distal (or lower) circumferential tubular portion or sleeve 32, which are spaced apart from each other. Proximal and distal sleeves 30 and 32, respectively, are adapted and proportioned to receive the respective spring 20 and drawstring 18, see FIG. 1A in combination with FIG. 2. A linear portion (not shown) weakened by perforation, scoring, or the like, extends circumferentially around the mouth 26 and is operably disposed between the proximal and lower sleeves 30 and 32. The scored portion is adapted to tear when the drawstring 18 is pulled with sufficient force so as to close the mouth 26 of the pouch 4 distal to the perforation, thereby providing fast detachment of pouch 4 from the spring member 20 simultaneously with closure of mouth 26. One skilled in the art will appreciate that alternative methods also can be utilized to detach the pouch 4 from the spring member 20, such as by pulling with a grasper or by cutting with a scissors.

With continued reference with FIG. 2, upper portion 26 includes one or more axial telescopic convolutions or folds 34 that are movable (e.g., expand longitudinally) from a folded configuration (FIGS. 1A and 1B) to an unfolded configuration (FIG. 1C) when a predetermined force is applied to a portion of the pouch 4. For illustrative purposes, two convoluted folds 34a and 34b are shown. More particularly, fold 34a serves as an outer fold and fold 34b serves as an inner fold; the significance of which described in greater detail below. Folds 34a and 34b are configured to accommodate retrieval of various tissue specimens, e.g., lengths of small intestine. With this purpose in mind, the folds 34a and 34b may be coupled to the pouch 4 and/or each other by one or more suitable coupling methods including, but not limited to adhesive, thermoforming, RF welding, etc. In the illustrated embodiment, the folds 34a and 34b are "tacked" or coupled to one another by either adhesive or thermosetting. When a predetermined pull force "Pf" is applied to the folds 34a and 34b, the folds 34a and 34b separate from one another for lengthening the pouch 4 (FIG. 1C). The type of adhesive (or amount thereof applied to couple the folds 34a and 34b to one another) may be chosen (or varied) to allow the outer fold 34a to separate first, then the inner fold 34b thereafter. A length of an unfolded pouch 4 is proportional to the number of axial folds 34. Accordingly, to vary a length of the pouch 4 in the unfolded state, the number of folds 34 may be respectively increased or decreased. For example, in certain embodiments, it may prove useful to utilize a pouch 4 that includes 3, 4, 5, etc. folds 34. Moreover, a length of each of the folds 34 may be varied to accommodate various surgical procedures and/or specific tissue specimens. For example, in one particular embodiment, fold 34a may include a length that is longer (or shorter) than a length of the fold 34b. In this instance, if the length of the first fold 34a is sufficient to accommodate a specific tissue specimen, than the fold 34b need not be unfolded.

Folds 34a and 34b are configured such that an area between the folds 34a and 34b is distributed (or otherwise configured) to provide a gradual or staggered separation between the folds 34a and 34b when a predetermined force is applied, e.g., adjacent the closed end 28, to the pouch 4. Specifically, the folds 34a and 34b expand longitudinally in stages as required to accommodate various specimen lengths. More specifically, when a specimen is grasped and, subsequently, positioned and/or "pulled" inside the pouch 4, the pull force "Pf" that is required to unfold the fold 34a, i.e., the outer fold, for lengthening the pouch 4 is less than the pull force "Pf" that is required to unfold the fold 34b, i.e., the inner fold. To ensure that the folds 34a and 34b gradually separate, the folds 34a and 34b may be held together or maintained in the "folded" configuration via one or more suitable types of holding features that may be operably associated with the folds 34a and 34b. For example, and in one particular embodiment, one or more suitable adhesives or the like, e.g., a low tack or double sided adhesive, may be operably coupled (with varied area of attachment) to one or both of the folds 34a and 34b. Alternatively, one or more locking features, e.g., one or more lock buttons, may be operably coupled to one or both of the folds 34a and 34b via one or more suitable coupling methods, e.g., thermoforming (or the like), or other suitable methods.

In the unfolded configuration, the folds 34a and 34b (and/or the overall shape or the walls of the pouch 4) taper toward the lower portion 28 (FIGS. 1C and 3). The angel at which the folds 34a and 34b tapers may be varied to accommodate various pull force "Pf" requirements, described in greater detail below. In the illustrated embodiment, folds 34a and 34b include a taper angle that ranges from about 0-15 degrees.

Lower portion 28 is in operative communication with the fold 34a. A proximal end 36 of the lower portion 28 tapers or narrows to a distal end 38 thereof. Distal end 38 of the lower portion 28 includes an elongated, generally circumferential configuration with a diameter that is less than the diameter of the upper portion 26 including the folds 34a and 34b when the folds 34a and 34b are in the unfolded configuration, see FIGS. 1A and 2.

One or more gripping features 40 are operably disposed along an interior of the pouch 4. In the illustrated embodiment, a plurality of spikes 40 is operably disposed at predetermined locations along an interior wall 42 of bottom portion 28. The spikes 40 are utilized to grasp, engage or otherwise attach to a specimen. More particularly, spikes 40 are configured to "grasp" or "pull" the specimen inside the pouch 4 when an exterior, e.g., exterior wall of the pouch 4 is compressed. To this end, the spikes 40 are shown having a generally triangular or pyramidal configuration with a base 41 and four walls 44 (two walls shown in the representative drawings) that extend inward toward a center of the pouch 4 and culminate to a tip 48. Tip 48 may be hooked, barbed, or may include one or more additional features, devices, or structures to facilitate "gripping" and/or "pulling," the specimen. As can be appreciated, different gripping features may be utilized to achieve the purposes described herein.

An internal surface of the pouch 4 may be coated with or made from a material that is "slippery" or includes a low friction coefficient, e.g., polytetrafluoroethylene, commonly referred to in the art and sold under the trademark TEFLON®. In certain embodiments, the internal surface of the upper portion 26 is coated with a hydrogel 50 (represented by hatching in FIG. 2) that may include a friction coefficient Fμ that may be in the range from about 0.003 to about 0.1. The hydrogel coating 50 is configured to allow for a substantially smaller pull force "Pf" that is required to "pull" the specimen inside the pouch 4, while increasing normal reaction forces $N_R$ acting on the exterior walls of the pouch 4 so that the pouch 4 is easier to stretch. Thus, a coating of hydrogel 50 having a low friction coefficient Fμ, and relatively small taper angle (e.g., 0-15 degrees) of the folds 34a and 34b (or the walls of the pouch 4), amplifies hoop stresses (i.e., stresses directed at the periphery of the opening 26 and/or the folds 34a and 34b) on the pouch 4 and a specimen assuring maximum compression thereof. The increased hoop stresses provides maximum compacting of tissue within the pouch 4 such that smaller diameter tissue is maintained within the pouch 4, which, in turn, prevents tissue from "bunching-up" in the pouch 4. Accordingly, this configuration of the pouch 4 provides an advantage of requiring a relatively smaller incision (for retrieval) being created within tissue of a patient when compared to known pouch assemblies.

With reference to FIG. 3, a force vector diagram illustrates the effect of a low friction coefficient Fμ inside of the pouch 4. That is, the friction coefficient Fμ between the internal wall of the pouch 4 that is coated with a hydrogel 50 and tissue positioned within the pouch 4. A relation of the pull force "Pf" or normal force $N_R$ as a function of the friction coefficient Fμ for a given angle of taper from the folds 34a and 34b to the bottom portion 28 is defined by:

$$P_f(\mu) = 2 \cdot \mu \cdot N_R \cdot \cos(\alpha)$$

where Pf is the "pull force," $N_R$ is the normal reaction force, a is the angle of taper from the folds 34a and 34b to the bottom portion 28, and μ is the friction coefficient for a given coating of hydrogel 50 (or other lubricious material).

Alternatively, a relation of the normal force $N_R$ as a function of the friction coefficient Fμ for a given angle of taper from the folds 34a and 34b to the bottom portion 28 is defined by:

$$N_R(\mu) = P_f / 2 \cdot \mu \cdot \cos(\alpha)$$

where Pf is the "pull force," $N_R$ is the normal reaction force, a is the angle of taper from the folds 34a and 34b to the bottom portion 28, and Fμ is the friction coefficient for a given coating of hydrogel 50

The angle α at which the folds 34a and 34b tapers toward the bottom portion 28 may range from about 0° to about 15°. Thus, a pouch 4 that includes an interior wall coated with a hydrogel 50 having a friction coefficient Fμ of 0.05 and an overall taper angle α equal to 5 degrees, and assuming that the normal reaction force $N_R$ required to stretch the pouch 4 is 5 lb., the "pull" force Pf is approximately equal to 0.5 lbs.

FIG. 4 illustrates the normal reaction force $N_R$ acting on the inner wall of the pouch 4 as a function of friction coefficient μ that ranges from 0.04-0.1. The normal reaction force $N_R$ acting on the interior walls of the pouch 4 and/or tissue positioned within the pouch 4 is amplified as a function of a decreased friction coefficient μ. For example, a pouch 4 that includes an interior wall coated with a hydrogel 50 having a friction coefficient Fμ of 0.05 and an overall taper angle α equal to 10 degrees, and assuming a 1.0 lb. "pull" force "Pf," the normal reaction force $N_R$ required to stretch the pouch 4 is 10 lb. Thus, a 1.0 lb. "pull" force "Pf" generates about 10 times greater reaction force $N_R$ on the interior walls of the pouch 4 and/or tissue positioned within the pouch 4 for a given hydrogel 50 coating. As can be appreciated, a coating of hydrogel 50 may be applied to an outside wall of the pouch 4 and configured to facilitate pulling tissue out of the pouch 4, i.e., the force required to pull out the tissue from the pouch 4 is reduced.

In use, a tissue specimen, e.g., tissue from the intestinal region, is placed in the pouch 4. A pull force "Pf" of suitable proportion, e.g., 1 lb., is applied to the distal end 38 of the pouch 4 which, in turn, causes the first fold 34a to "break free" or release from the folded position, see FIG. 5. That is, the pouch 4 is in a semi-folded (or unfolded) position. When the distal end 38 is pulled, the spikes 40 "engage" and "pull" the tissue specimen with the distal end 38 of the pouch 4. A continued pulling force causes the second fold to "break free" or release from the folded position such that the pouch 4 is in a fully unfolded condition, see FIG. 1C, for example.

From the foregoing and with reference to the various figure drawings, those skilled in the art will appreciate that certain modifications can also be made to the present disclosure without departing from the scope of the same. For example, it may prove useful to include a grasping device or structure on the pouch 4. Specifically, a pouch ring 52 (shown in phantom for illustrative purposes) may be operably positioned on the pouch 4 and configured to facilitate grasping the pouch 4 when tissue is positioned therein. More specifically, the pouch ring 52 may be operably coupled to a distal end of the bottom portion 28 of the pouch 4.

In certain instances, to facilitate grasping of the pouch 4, the lower portion 28 of the pouch 4 may be thicker than the upper portion 26 of the pouch 4 or the lower portion 28 of the pouch 4 may be textured or otherwise treated.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A specimen retrieval device, comprising
an applicator including a handle assembly; and
a specimen retrieval pouch operably disposed within the applicator and deployable therefrom upon actuation of the handle assembly, the specimen retrieval pouch including a closed bottom portion and an open upper portion, the closed bottom portion including a plurality of retention features circumferentially disposed on an inner annular side wall of the closed bottom portion, the plurality of retention features configured to engage a specimen positioned within the confines of the closed bottom portion when the closed bottom portion is pulled distally, wherein the plurality of retention features are in the form of a plurality of spikes.

2. A specimen retrieval device according to claim 1, wherein the open upper portion includes at least one axial fold movable from a folded configuration to an unfolded configuration when a predetermined force is applied to pull the closed bottom portion of the specimen retrieval pouch.

3. A specimen retrieval device according to claim 1, wherein the plurality of retention features extends in an orthogonal orientation from the inner annular wall of the specimen retrieval pouch and toward a center thereof.

4. A specimen retrieval device according to claim 1, wherein an interior surface of the specimen retrieval pouch is coated with a lubricious material.

5. A specimen retrieval device according to claim 4, wherein the lubricious material is selected from the group consisting of a hydrogel gel and polytetrafluoroethylene.

6. A specimen retrieval device according to claim 4, wherein the lubricious material provides a friction coefficient that ranges from about 0.003 to about 0.09.

7. A specimen retrieval device according to claim 1, wherein the open upper portion includes at least two axial folds.

8. A specimen retrieval device according to claim 7, wherein the at least two axial folds include an outer axial fold and an inner axial fold, wherein a force needed to move the outer axial fold from a folded configuration to an unfolded configuration is less than a force needed to move the inner axial fold from a folded configuration to an unfolded configuration.

9. A specimen retrieval device according to claim 1, wherein the plurality of retention features are configured to engage the specimen positioned within the confines of the closed bottom portion when the closed bottom portion is pulled distally with a pulling force that is applied in a generally parallel orientation with respect to a longitudinal axis defined through the specimen retrieval pouch.

10. A specimen retrieval device according to claim 1, wherein the plurality of spikes include one of a generally triangular configuration.

11. A specimen retrieval device according to claim 1, further including a grasping device configured to facilitate grasping the specimen retrieval pouch.

12. A specimen retrieval device according to claim 11, wherein the grasping device is in the form of a pouch ring that is positioned on an exterior surface of the specimen retrieval pouch adjacent the closed bottom portion.

* * * * *